US009180077B2

(12) United States Patent
Lambelet et al.

(10) Patent No.: US 9,180,077 B2
(45) Date of Patent: Nov. 10, 2015

(54) GREEN TEA EXTRACTS OF IMPROVED BIOAVAILABILITY

(75) Inventors: Pierre Lambelet, Saint-Legier (CH);
Karlheinz Bortlik, Syens (CH);
Magalie Sabatier, Lausanne (CH);
Vanessa Crespy, Dublin, OH (US);
Gary Williamson, Harrogate Yorkshire (GB)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 13/322,802

(22) PCT Filed: May 28, 2010

(86) PCT No.: PCT/EP2010/057431
§ 371 (c)(1),
(2), (4) Date: Feb. 28, 2012

(87) PCT Pub. No.: WO2010/136570
PCT Pub. Date: Dec. 2, 2010

(65) Prior Publication Data
US 2012/0177738 A1    Jul. 12, 2012

(30) Foreign Application Priority Data

May 29, 2009    (EP) .................................... 09161493

(51) Int. Cl.
| | | |
|---|---|---|
| *A01N 43/16* | (2006.01) |
| *A61K 8/49* | (2006.01) |
| *A23F 3/16* | (2006.01) |
| *A23L 1/30* | (2006.01) |
| *A23L 1/302* | (2006.01) |
| *A61K 8/67* | (2006.01) |
| *A61K 8/97* | (2006.01) |
| *A61K 36/82* | (2006.01) |
| *A61Q 17/04* | (2006.01) |
| *A61Q 19/00* | (2006.01) |
| *A61Q 19/08* | (2006.01) |

(52) U.S. Cl.
CPC .................. *A61K 8/498* (2013.01); *A23F 3/163* (2013.01); *A23L 1/3002* (2013.01); *A23L 1/302* (2013.01); *A61K 8/676* (2013.01); *A61K 8/97* (2013.01); *A61K 36/82* (2013.01); *A61Q 17/04* (2013.01); *A61Q 19/00* (2013.01); *A61Q 19/005* (2013.01); *A61Q 19/007* (2013.01); *A61Q 19/08* (2013.01); *A23V 2002/00* (2013.01); *A61K 2800/52* (2013.01); *A61K 2800/92* (2013.01)

(58) Field of Classification Search
None
See application file for complete search history.

(56) References Cited

U.S. PATENT DOCUMENTS 5,470,874 A    11/1995    Lerner 6,228,387 B1    5/2001    Borod
6,235,272 B1    5/2001    Greene
2006/0057230 A1    3/2006    Chow

FOREIGN PATENT DOCUMENTS

| | | |
|---|---|---|
| JP | 09252746 | 9/1997 |
| JP | 2000159669 | 6/2000 |
| JP | 2003024010 | 1/2003 |
| JP | 2005021098 | 1/2005 |
| JP | 2007191426 | 8/2007 |
| JP | 2008094754 | 4/2008 |
| JP | 2008178401 | 8/2008 |
| JP | 2008273979 | 11/2008 |
| JP | 2009055905 | 3/2009 |
| KR | 20000058730 | 10/2000 |
| WO | 9933439 | 7/1999 |
| WO | 0105367 | 1/2001 |
| WO | 2006000226 | 1/2006 |
| WO | 2006124033 | 11/2006 |
| WO | 2007017037 | 2/2007 |

OTHER PUBLICATIONS

"PRO-C: Advanced Free Radical Protection Formula," Health Products Distributors, Inc., PRO-C, webpage archived on Sep. 22, 1999 (2 pages) available at http://web.archive.org/web/19990922013540/http://www.integratedhealth.com/hpdspec/proc.html.*
Richelle et al, "Skin Bioavailability of Dietary Vitamin E, Carotenoids, Polyphenols, Vitamin C, Zinc and Selenium," British Journal of Nutrition, vol. 96, Issue 2, pp. 227-238 (2006).*
Zhu et al, "Stabilizing Effect of Ascorbic Acid on Flavan-3-ols and Dimeric Procyanidins from Cocoa," Journal of Agricultural and Food Chemistry, vol. 51, No. 3, pp. 828-833 (2003).*
Zhen-Yu Chen: "Stabilizing effect of ascorbic acid on green tea catechins," J. Agric. Food Chem., [Online] Jun. 26, 1998, XP002548184; Retrieved from the Internet: URL:http://pubs.acs.org/doi/pdf/10.1021/jf971022g>, [retrieved on Sep. 29, 2009], the whole document.
Anonymous: "MICROgenics Complete antioxidant," [Online] May 24, 2008, XP002548181; Retrieved from the Internet: URL:http://www.micro-genics.com.au/product/ complete-antioxidant.html>, [retrieved on Sep. 30, 2009], the whole document.
Anonymous: "PRO-C : synergistic antioxidants plus vitamin C formula," [Online] Jun. 29, 2008, XP002548180; Retrieved from the Internet: URL:http://www.integratedhealth.com/hpdspec/proc.html>, [retrieved on Sep. 29, 2009], the whole document.
PCT International Search Report for Application No. PCT/EP2010/057431 with a Mailing Date of Aug. 6, 2010, 4 Pages.
Hu et al. "Antioxidant Activity of a Proanthocyanidin-Rich Extract from Grape Seed in Whey Protein Isolate Stabilized Algae Oil-in-Water Emulsions" Journal of Agricultural and Food Chemistry, vol. 52, 2004, pp. 5272-5276.

(Continued)

*Primary Examiner* — Dennis J Parad
(74) *Attorney, Agent, or Firm* — K&L Gates LLP

(57) ABSTRACT

The present invention relates to a green tea formulation stabilized by natural antioxidants such as OPC together with vitamin C or vitamin C analogs. The invention also relates to the use of a mixture of OPC and ascorbic acid to increase bioavailability of green tea catechins. It also relates to a food, pharmaceutical or cosmetic composition that contains the stabilized green tea formulation.

10 Claims, 3 Drawing Sheets

(56) References Cited

OTHER PUBLICATIONS

Hara et al. "Evaluation of Anti-oxidative Activities of South African Herbal Tea and Grape Seed Extracts" Journal of Oleo Science, vol. 54, No. 12, 2005, pp. 627-632.

Spranger et al. "Chemical characterization and antioxidant activities of oligomeric and polymeric procyandin fractions from grape seeds" Science Direct Food Chemistry, vol. 108, 2008, pp. 519-532.

Murphy et al. "Dietary flavanols and procyanidin oligomers from cocoa (*Theobroma cacao*) inhibit platelet function" American Journal of Clinical Nutrition, vol. 77, 2003, pp. 1466-1473.

\* cited by examiner

GREEN TEA EXTRACTS OF IMPROVED BIOAVAILABILITY

CROSS REFERENCE TO RELATED APPLICATIONS

The present application is a National Stage of International Application No. PCT/EP2010/057431, filed on May 28, 2010, which claims priority to European Patent Application No. 09161493.3, filed on May 29, 2009, the entire contents of which are being incorporated herein by reference.

The present invention relates to a green tea formulation stabilized by natural antioxidants such as oligomeric procyanidins (OPC) together with vitamin C or vitamin C analogs. The invention also relates to the use of a mixture of OPCs and ascorbic acid to increase bioavailability of green tea catechins and maximize the beneficial health effect of the catechins. It also relates to a food, a pet food, a food supplement, pharmaceutical or cosmetic composition that contains the stabilized green tea formulation.

BACKGROUND OF THE INVENTION

Green tea, the most commonly consumed beverage in the world after water, offers some important health benefits. The compounds believed to be responsible for these benefits are polyphenols and in particular catechins.

The major green tea polyphenols (flavan-3-ol) are catechins, i.e. (+)-catechin (C) and its stereoisomer and four derivatives, namely (−)-epicatechin (EC), (−)-epigallocatechin (EGC), (−)-epigallocatechin-3-gallate (EGCg), (−)-epicatechin-3-gallate (ECg).

Although amounts of catechins vary depending on the factors influencing plant metabolism such as light, rain fall, temperature, nutrient availability, leaf age, and genetic make-up, they usually constitutes 20-30% of the dry matter of fresh green tea leaves. Catechins represent approximately 80% of the total polyphenol content of green tea. As they are rarely destroyed during manufacturing of green tea, catechins are a major part of commercial green tea extracts.

Green tea catechins display several health benefits that are often associated to their antioxidant activities including scavenging of reactive oxygen and nitrogen species, free metal chelation, inhibition of transcriptional factors and inhibition of oxidative enzymes such as lipoxygenase and cycloxygenase.

The health effects of polyphenols depend on the amount consumed and on their bioavailability. However their bioavailability is poor, which seems to be linked to a particular instability of these compounds under physiological conditions.

One possible strategy to increase the stability of green tea catechins under adverse conditions is to protect them by antioxidants thus preventing the chemical changes caused by exposure to oxygen. For example, Rode et al. (2002) have shown that the incorporation of a hydrosoluble antioxidant (vitamin C) stabilized green tea catechins in emulsions but they did not see any effect when they used lipophilic antioxidants such as butylated hydroxytoluene or propyl gallate. Indeed, all four catechin species and, in particular, EgC and EgCg were found to be stabilized in the presence of ascorbic acid and this protection is dose-dependent. Even though this protective effect of ascorbic acid has long been known, its effect on bioavailability has never been confirmed. In fact in G. Williamson et al., Int. J. Vitam. Nutri Res. 77 (3) 2007, 224-235, it has been recently showed that the addition of antioxidant (vitamins and carotenoids) had no effect on bioavailability of polyphenols such as catechins.

It is thus an object of the present invention to address the above problems by providing a formulation that contains catechins with improved stability and increased bioavailability. It is also an object of the present invention to provide a green tea formulation that has an increased bioavailability which can be used for applications in food or pet food products, nutritional or food supplements, cosmetic or pharmaceutical preparations.

SUMMARY OF THE INVENTION

Accordingly, it is a first object of the invention to provide the use of a mixture of oligomeric procyanidins (OPC) and ascorbic acid or vitamin C analogs for the preparation of a product to increase the bioavailability of catechins, in particular green tea catechins.

Advantageously, the composition has an improved stability and bioavailability of its catechins content. Moreover, the composition has an enhanced nutritional value, in the form of a better bioavailability and stability. It can be used directly or concentrated or dried into powder for several applications into daily-consumed food products or other nutritional uses.

It is a further object of the invention, to provide a food, a pet food, a cosmetic preparation, a nutritional supplement or a pharmaceutical preparation containing the formulation according to the invention.

In a further aspect, the invention provides a method for increasing stability and bioavailability of green tea catechins using a combination of OPC and ascorbic acid.

It is a further object to provide the use of a formulation as described above for the preparation of an oral, cosmetic or pharmaceutical composition intended for improving skin health, in particular for photo protection of the skin or for protecting skin tissue against ageing.

It is still a further object to provide the use of a formulation as described above for the preparation of an oral, topical or pharmaceutical composition intended for weight management, cardiovascular diseases, type 2 diabetes, cognitive function or inflammation.

The present invention now makes available to the consumer an improved composition based on green tea catechins which has an increased bioavailability and bioefficacy.

FIGURES

The present invention is further described hereinafter with reference to some of its embodiments shown in the accompanying drawings wherein.

Figure 3:
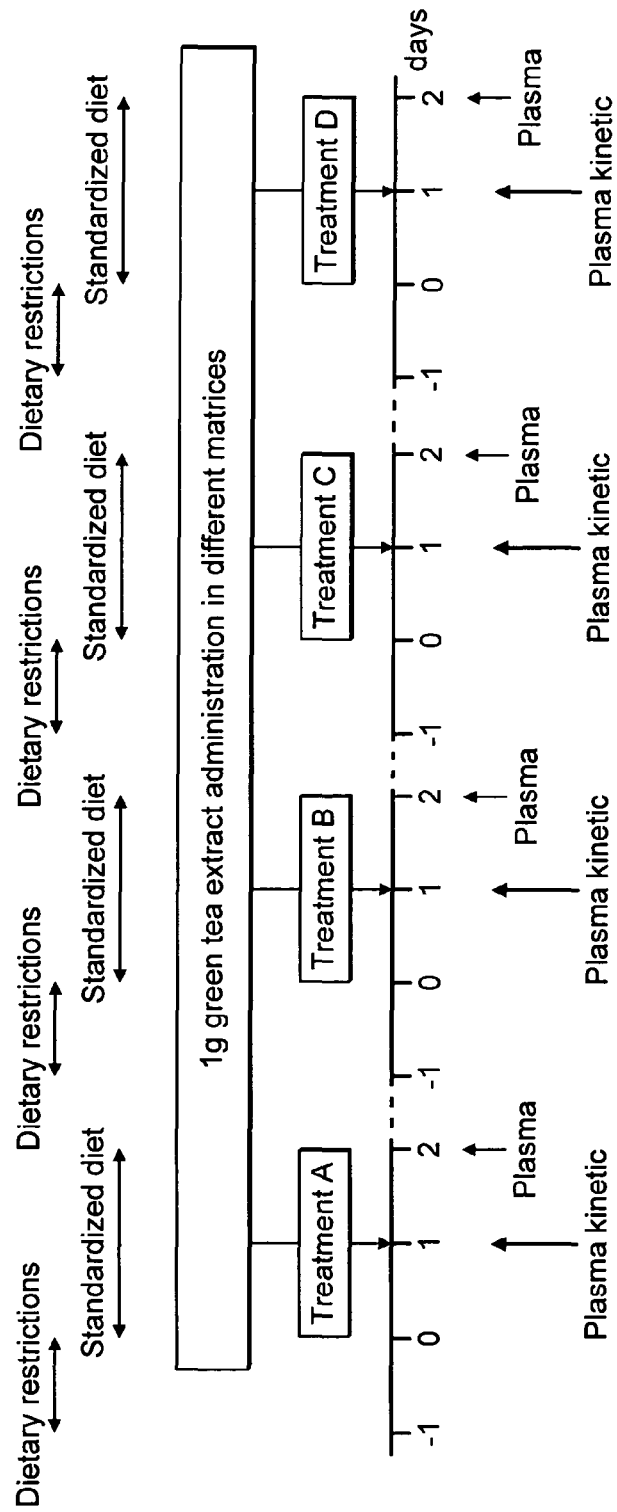

FIG. 3—design of the clinical study on green tea catechins administration

Figure 4:
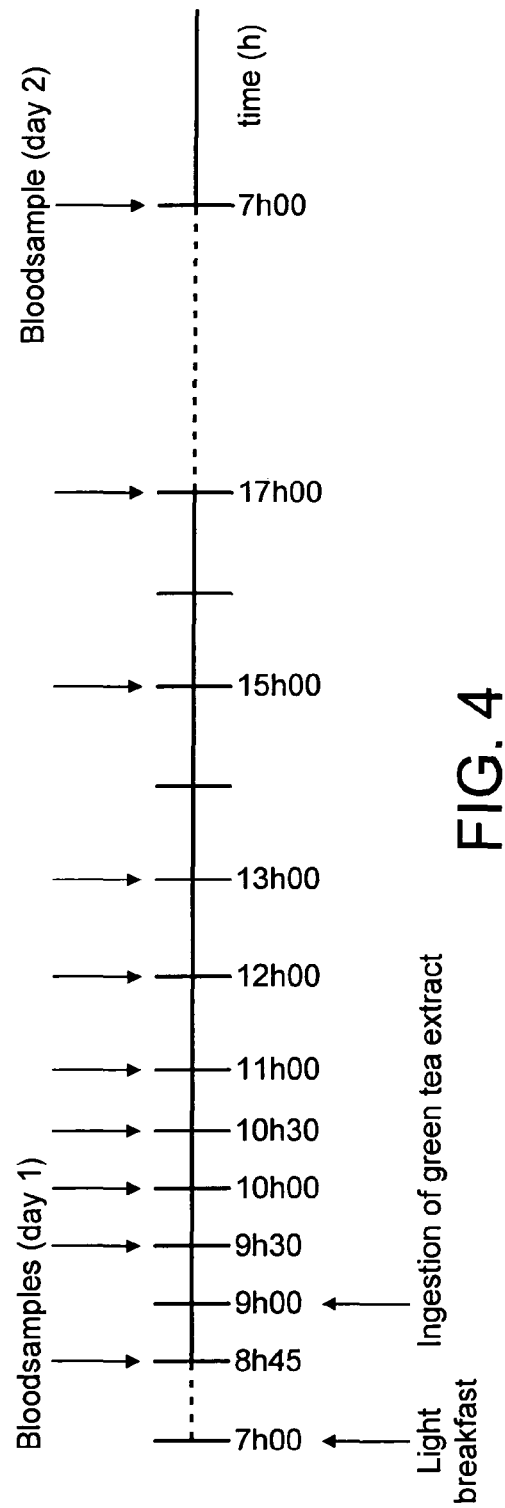

FIG. 4: Blood sampling for plasma pharmacokinetics for each treatment A, B, C, and D.

DETAILED DESCRIPTION OF THE INVENTION

Within the following description, the term "green tea catechins" is understood to mean catechin (C), epicatechin (EC), gallocatechin (GC), gallocatechin gallate (GCG), epigallocatechin (EGC), epicatechin gallate (ECg), epigallocatechin gallate (EGCg).

According to the first object, the use of a formulation containing catechins, which comprises a mixture of oligomeric procyanidins (OPC) and ascorbic acid to increase bioavailability of green tea catechins, is concerned.

In fact, upon screening of several molecules under physiological conditions, it has been surprisingly found that the addition of OPC and ascorbic acid (Vit C) or Vit C analogs (such as furaneol, etc. . . . ) to a formulation containing catechins will significantly improve the bioavailability of said catechins.

In a preferred embodiment, the catechins are from green tea. Other sources of catechins may be alternatively used e.g. wild plant fruits, in particular berries (cranberry, blackberry, blueberry, elderberry, service berry, chokeberry, quince, etc. . . . ), cocoa, beans or fruits Green tea (or other plant source) may be used in the form of fresh, concentrated or dried materials, for example, air or freeze dried material. The amount of catechins in the composition will depend upon the application of said formulation. In a preferred embodiment, the catechin content, in particular in the form of green tea extract, may be comprised between 1 and 50% and most preferably from 5 to 30%.

Preferably, the OPC are from grape source. In a preferred embodiment, they can be obtained from pine bark or grape seeds, for example. Also cocoa and wild berry extracts could be alternatively used as OPC source, as well as all known source of OPC.

Oligomeric procyanidins and ascorbic acid are added to the catechins in an amount sufficient to at least improve the bioavailability of catechins and/or to reduce or arrest the symptoms of a disorder that can be treated or prevented by the administration of catechins. An amount adequate to accomplished this is defined as "a therapeutically effective does". Amounts effective for this purpose will depend on a number of factors known to those skilled in the art such as the severity of the disease and/or the weight and general state of the patient. In prophylactic applications, compositions according to the invention are administered to a patient susceptible to or otherwise at risk of a particular disorder that can be treated or prevented by the administration of hesperetin in an amount that is sufficient to at least partially reduce the risk of developing a disease. Such an amount is defined to be "a prophylactic effective dose". Again, the precise amounts depend on a number of patient specific factors such as the patient's state of health and weight.

In a preferred embodiment, the composition contains 1 to 80% of grape seed extract, preferably 10 to 40%, depending on its OPC content which may vary from 60 to 99% of OPC in the grape seed extract. The ascorbic acid, or Vit C analog may be present in an amount from 0.1 to 15%, most preferably from 1 to 6% (with regard to the green tea extract).

According to a further aspect, the present invention relates to an oral composition comprising the formulation described above in a foodstuff, in a food supplement, in a pet food product, in a cosmetic preparation or in a pharmaceutical preparation.

In a preferred embodiment, a food composition for human consumption is supplemented by the above composition. This composition may be a nutritional complete formula, a dairy product, a chilled or shelf stable beverage, a powdered beverage, a mineral or purified water, a liquid drink, a soup, a dietary supplement, a meal replacement, a nutritional bar, a confectionery, a milk or a fermented milk product, a yoghurt, a milk based powder, an enteral nutrition product, an infant formula, an infant nutritional product, a cereal product or a fermented cereal based product, an ice-cream, a chocolate, coffee, a culinary product such as mayonnaise, tomato puree or salad dressings or a pet food.

For ingestion, many embodiments of oral compositions and in particular of food supplements are possible. They are formulated by means of the usual methods for producing sugar-coated tablets, pills, pastes, gums, gelatine capsules, gels, emulsions, tablets, capsules or drinkable solutions or emulsions, which can then be taken directly with water or by any other known means.

Also, the formulation as described above may be incorporated into any other forms of food supplements or of enriched foods, for example food bars, or compacted or non-compacted powders. Methods for preparing them are common knowledge.

The food composition or food supplement may also include a sweetener, a stabilizer, an antioxidant, an additive, a flavouring or a colorant. The composition may also contain synthetic or natural bioactive ingredients such as amino acids, fatty acids, vitamins, minerals, carotenoids, polyphenols, etc. that can be added either by dry or by wet mixing to said composition before pasteurization and/or drying.

According to an embodiment, the composition of the invention may be used cosmetically. By "cosmetic use" is meant a non-therapeutic use which may improve the aesthetic aspect or comfort of the skin, coat and/or hair of humans or pets.

When used cosmetically, the food composition or supplement of the invention may assume any form of food composition or supplement described above. Preferably, it is in the form of dietary supplements, which may be in liquid or dry form, such as solutions, sprays, tablets, capsules, gelatine capsules, lozenges, powders, gels, emulsions etc. More preferably it is in the form of a capsule. A supplement for cosmetic purpose can additionally comprise a compound active with respect to the skin.

The amount of the formulation or food composition or food supplement to be consumed by the individual to obtain a beneficial effect will also depend upon its size, its type, and its age.

In another embodiment, a pharmaceutical composition can be administered for prophylactic and/or therapeutic treatments. In therapeutic applications, compositions are administered to a patient already suffering from a disease, as described herein under, in an amount sufficient to cure or at least partially arrest the symptoms of the disease and its complications. An amount adequate to accomplish this is defined as "a therapeutically effective dose". Amounts effective for this will depend on the severity of the disease and the weight and general state of the patient. In prophylactic applications, compositions according to the invention are administered to a patient susceptible to or otherwise at risk of a particular disease. Such an amount is defined to be "a prophylactic effective dose". In this use, the precise amounts again depend on the patient's state of health and weight.

The compounds of the invention are preferably administered with a pharmaceutically acceptable carrier, the nature of the carrier differing with the mode of administration, for example, enteral, oral and topical (including ophthalmic) routes. The desired formulation can be made using a variety of excipients including, for example, pharmaceutical grades of mannitol, lactose, starch, magnesium stearate, sodium saccharin, cellulose, magnesium carbonate. This composition may be a tablet, a capsule, a pill, a solution, a suspension, a syrup, a dried oral supplement, a wet oral supplement.

It will be appreciated that the skilled person will, based on his own knowledge select the appropriate components and galenic form to target the active compound to the tissue of interest, e.g. the skin, colon, stomach, eyes, kidney or liver, taking into account the route of administration.

The invention also relates to a topical cosmetic use of the formulation described above. It may be formulated in lotions, shampoos, creams, sun-screens, after-sun creams, anti-ageing creams and/or ointments, for example. This composition which can be used topically additionally comprises a fat or an oil which can be used in cosmetics, for example those mentioned in the CTFA work, Cosmetic Ingredients Handbook, Washington. It is also possible to add other cosmetically active ingredients. The composition additionally comprises a structuring agent and an emulsifier. Other excipients, colorants, fragrances or opacifiers can also be added to the composition. It will be appreciated that the present cosmetic products will contain a mixture of different ingredients known to the skilled person, ensuring a fast penetration of the said substance into the skin and preventing degradation thereof during storage.

It will be understood that the concept of the present invention may likewise be applied as an adjuvant therapy assisting in presently used medications. Since the compounds of the present invention may easily be administered together with food material special clinical food may be applied containing a high amount of the said substances. It will be clear that on reading the present specification together with the appending claims the skilled person will envisage a variety of different alternatives to the specific embodiments mentioned herein.

The product of the present invention may be used to increase effectiveness of the catechins. Catechins are for example known to improve skin health, to have positive effects in the prevention or treatment of cardiovascular diseases, type 2 diabetes, cognitive function or inflammation. They can also be used for weight management reduction. Consequently, the oral composition of the present invention may be used to improve skin health, in particular for photo protection of the skin or for protecting skin tissue against ageing. Also, to slow down the ageing of the skin, for example. It may also be useful in the prevention or treatment of sensitive, dry or reactive skins, or for improving skin density or firmness.

The effect of the compositions according to the present invention, on skin of humans or pets, can be measured by using conventional methods including minimal erythemal dose (MED), colorimetry, transepidermal water loss, DNA repair, measure of interleukins and proteoglycans production, or collagenase activity, barrier function or cell renewal.

The present invention is further illustrated by means of the non-limiting examples described below.

EXAMPLES

Example 1

Stability Study of Green Tea Catechins

Material and Methods

Commercial green tea extracts (instant green tea TCTG) were obtained from Choladi factory (Cherambadi, India). They were prepared by water extraction from green leaf at 90° C. followed by spray-drying. Two batches were used. Their catechins profiles are reported in Table I.

TABLE I

Catechins contents of Choladi green tea extracts

| Batch | Amount [% of powder] | | | | | |
|---|---|---|---|---|---|---|
| | EgC | C | EgCg | EC | ECg | Total |
| 1 | 7.4 | 0.3 | 7.8 | 2.3 | 1.1 | 18.9 |
| 2 | 10.6 | 0.4 | 13.3 | 2.6 | 1.7 | 28.6 |

Different qualities of grape seed OPC (oligomeric procyanidins) were received from Indena (Milan, Italy), Kikomann (Noda-City, Japan) for Gravinol product series and from DRT (Dax, France) for Vitaflavan 50. Pine bark OPC (Oligopin) was a gift from DRT (Dax, France).

Furaneol (4-Hydroxy-2,5-Dimethyl-3(2H)-Furanone), homofuraneol, furaneolmethylether and norfuraneol were purchased from Givaudan (Dübendorf, Switzerland). Vitamin C, maltol, cysteine and metabisulfite were from Sigma-Aldrich (Buchs, Switzerland).

Sodium stearoyl lactylate (SSL) and diacetyl tartaric acid esters of monoglycerides (Datem) were from Danisco (Copenhagen, Denmark).

Sodium dihydrogen phosphate monohydrate and di-sodium hydrogen phosphate dihydrate were from Merck (Darmstadt, Germany).

Standards of catechins used for HPLC calibration were obtained from Extrasynthese (Genay; France).

Samples were prepared according to the following method. Briefly, each sample was treated with acetic acid (30% final concentration) for 30 min and then added to an aqueous solution containing 10% acetonitrile, 0.5 mg/mL EDTA and 0.5 mg/mL ascorbic acid. The mix was then centrifuged for 30 min at 14'000×g and the supernatant analysed by HPLC. Following this protocol allows the complete recovery of all catechins.

Green tea catechins were determined by reverse phase HPLC using an analytical method based on the ISO FDIS 14502-2 method. The HPLC system used was a 1100 series Hewlett-Packard (Geneva, Switzerland) model equipped with an ultraviolet-visible photodiode array and a fluorimetric detector. Catechins were detected by UV absorption at 280.4 nm except for catechins and epicatechin that were detected by fluorescence (excitation: 280 nm; emission: 310 nm). Samples (10 µl) were separated on a Zorbax RX—C18 column (4.6 mm internal diameter×250 mm length, Agilent technologies). The separation was achieved at room temperature using the gradient reported in Table II. Flow rate was 1.0 mL/min.

TABLE II

Solvent gradient used for the HPLC separation of catechins.

| Time [min] | Solvent B [%] |
|---|---|
| 0 | 10 |
| 10 | 11 |
| 32 | 27 |
| 32.1 | 50 |
| 35 | 50 |
| 35.1 | 10 |
| 45 | 10 |

Solvent A: water containing 0.05% trifluoroacetic acid (TFA);
solvent B: mixture of MeOH and acetonitrile (60:40) containing 0.05% TFA.

Sample concentration of green tea catechins (C, EC, EgC, EgCg, ECg) were calculated based on the corresponding calibration curve and reported as % of the initial value (sample at t0). Since caffeine, endogenous to green tea samples, is stable under the selected assay conditions, it was used as internal standard for all calculations. Thus caffeine concentration found in fresh green tea extract was used for data normalisation.

Green tea and antioxidants or corresponding formulations were dispersed in buffer at pH 7.4 (Na—Pi, 100 mM) and assayed under standardized conditions (in open containers, constant stirring at 37° C.) for up to 24 h. At defined time intervals individual aliquots were collected and samples for HPLC injection were prepared as stated above.

Results

Stabilisation of Green Tea Extract with Vitamin C

Vitamin C is known to be a powerful antioxidant and to prevent catechin degradation when added to green tea. In order to get an idea on the minimal concentration of vitamin C necessary to achieve protection of catechins, green tea extracts containing increasing amounts of vitamin C have been incubated for up to 24 h. Since the objective of this work is to achieve maximal protection of catechins under physiological conditions, incubation parameters were selected to be comparable with the conditions that could be found in the intestine, i.e. pH 7.4 at 37° C.

TABLE III

Dose-dependent catechin retention in green tea samples containing increasing concentration of vitamin C incubated for up to 24 h. (C = catechin, EC = epicatechin, EgC = epigallocatechin, EgCg = epigallocatechin-3-gallate, ECg = epicatechin-3-gallate)

| sample GTE 0.1% + | | catechin retention | | | | |
|---|---|---|---|---|---|---|
| vitamin C (mM) | incubation time (h) | EgC | C | EgCg | EC | ECg |
| | | | (% of initial value) | | | |
| control | 2 | 0 | 104 | 1 | 89 | 77 |
| | 6 | 0 | 54 | 0 | 25 | 9 |
| | 24 | 0 | 0 | 0 | 0 | 0 |
| 0.1 | 2 | 0 | 106 | 3 | 90 | 81 |
| | 6 | 0 | 53 | 0 | 26 | 9 |
| | 24 | 0 | 0 | 0 | 0 | 0 |
| 0.5 | 2.0 | 88 | 110 | 90 | 92 | 97 |
| | 6 | 0 | 82 | 0 | 46 | 26 |
| | 24 | 0 | 0 | 0 | 0 | 0 |
| 1.0 | 2 | 92 | 108 | 94 | 93 | 97 |
| | 6 | 20 | 126 | 41 | 83 | 87 |
| | 24 | 0 | 0 | 0 | 1 | 0 |
| 2.5 | 2 | 92 | 108 | 95 | 94 | 97 |
| | 6 | 82 | 125 | 89 | 86 | 95 |
| | 24 | 0 | 172 | 1 | 64 | 53 |
| 5.0 | 2 | 93 | 107 | 94 | 93 | 97 |
| | 6 | 85 | 117 | 88 | 86 | 91 |
| | 24 | 62 | 175 | 69 | 75 | 78 |

As already known from previous investigations, EgC and EgCg are the most unstable catechins and they mostly degraded already after 2 h of incubation in the non-protected green tea extract (Table III). With the selected concentration, significant effects of vitamin C were visible only at concentration of 0.5 mM even though other experiments have shown that ascorbic acid at concentration of 0.2 mM already exerts a certain protection at least for 2 h of incubation (data not shown). Maximum protection at 2 h is obtained with a vitamin C concentration equal or superior to 1 mM, whereas the plateau is reached only at 2.5 mM for a stabilisation during 6 h. The other catechins are more stable under the selected conditions and after 6 h part of them could be still detected in the vitamin C-free sample.

Addition of ascorbic acid to the assays significantly improved also their stability in a dose dependent matter. Interestingly, in vitamin C-stabilised green tea (>1 mM), the amount of catechins (C) steadily increased during incubation to reach 175% of the initial value after 24 h. This time dependent generation of C was not investigated in detail, but it is well known that some catechins are prone to epimerisation. Continuous epimerisation of another catechin species into C and a delayed degradation of C by increasing concentrations of ascorbic acid could be one explanation for the increase of C upon time.

Vitamin C was found to be an efficient antioxidant for catechin protection. Assuming that intestinal absorption is completed after 2-3 h, concentration >0.2 mM is sufficient to already achieve maximal protection.

Effect on Stabilisation of Green Tea Catechins by Oligomeric Procyanidins (OPCs)+Vitamin C Extracts rich in OPCs are characterized by their oligomer or polymer content of catechins and the antioxidant activity attributed to these compounds. However, there are still considerable amounts of monomers present in these preparations depending on the raw material and process used for extraction. Indeed, OPC-rich extracts are known to contain at least catechin and epicatechin, two catechin species that are also present in green tea extracts. Since the addition of these extracts to green tea would significantly change the profile of catechins in the mixture, a characterization of the selected OPC extracts for their catechin monomer profile has been performed.

Analytical results confirmed that C and EC were the prevailing catechin species found in OPC preparations in amounts varying between 1% and 20% (w/w) of total sample (Table IV). EgC was absent in the extracts. In addition, small amounts of EgCg were found in the Indena grape seed OPC and in Oligopin pine bark OPC. ECg was observed in both of these extracts and in the Vitaflavan sample. All these three samples were particularly rich in catechin monomers.

TABLE IV

Monomer profile of catechins in commercial preparations rich in OPCs. (C = catechin, EC = epicatechin, EgC = epigallocatechin, EgCg = epigallocatechin-3-gallate, ECg = epicatechin-3-gallate)

| OPC-rich products | catechin and caffeine content (g/100 g of sample) | | | | | | |
|---|---|---|---|---|---|---|---|
| | EgC | C | caffeine | EgCg | EC | ECg | Tot |
| Oligopin | 0.0 | 4.3 | 0.0 | 0.1 | 0.8 | 0.3 | 5.4 |
| Vitaflavan 50 | 0.0 | 18.3 | 0.0 | 0.0 | 11.3 | 0.9 | 30.5 |
| Gravinol | 0.0 | 0.8 | 0.0 | 0.0 | 0.4 | 0.0 | 1.3 |
| Gravinol - T | 0.0 | 0.5 | 0.0 | 0.0 | 0.3 | 0.0 | 0.8 |
| Gravinol - S | 0.0 | 2.7 | 0.0 | 0.0 | 1.0 | 0.0 | 3.8 |
| Gravinol - SL | 0.0 | 2.4 | 0.0 | 0.0 | 1.2 | 0.0 | 3.6 |
| Indena | 0.0 | 16.0 | 0.03 | 0.2 | 11.7 | 1.5 | 29.5 |

Then, the effect on stability of green tea catechins was measured for different OPC/Vitamin C mixtures. It has been showed (Table V) that compared to the protection of vitamin C alone most combinations with OPC extracts showed a better retention of EgC and EgCg after 2 and 5 h.

The OPC preparation from Indena was retained for further optimisation trials.

TABLE V

Catechin protection in incubated green tea samples stabilized by vitamin C and OPC-rich extracts from different suppliers. (C = catechin, EC = epicatechin, EgC = epigallocatechin, EgCg = epigallocatechin-3-gallate, ECg = epicatechin-3-gallate)

| sample 0.5% OPC + 0.2 mM vitamin C | time of incubation (h) | EgC | C | EgCg | EC | ECg |
|---|---|---|---|---|---|---|
| | | | in % of initial value | | | |
| control (vit.C only) | 2 | 61 | 100 | 75 | 92 | 97 |
| Oligopin | 2 | 97 | 93 | 86 | 79 | 95 |
| Vitaflavan 50* | 2 | 91 | 97 | 89 | 95 | 98 |
| Gravinol | 2 | 63 | 94 | 77 | 94 | 91 |
| Gravinol - T | 2 | 33 | 95 | 54 | 93 | 94 |
| Gravinol - S | 2 | 70 | 96 | 83 | 102 | 98 |
| Gravinol - SL | 2 | 67 | 92 | 78 | 91 | 93 |
| Indena* | 2 | 99 | 103 | 85 | 100 | 101 |
| control (vit.C only) | 5 | 7 | 104 | 14 | 82 | 83 |
| Oligopin | 5 | 41 | 84 | 60 | 73 | 87 |
| Vitaflavan 50* | 5 | 63 | 87 | 66 | 85 | 89 |
| Gravinol | 5 | 22 | 85 | 34 | 79 | 83 |
| Gravinol - T | 5 | 2 | 79 | 9 | 73 | 74 |
| Gravinol - S | 5 | 19 | 83 | 44 | 86 | 85 |
| Gravinol - SL | 5 | 31 | 82 | 47 | 80 | 82 |
| Indena* | 5 | 73 | 98 | 64 | 94 | 94 |

Figure 1:
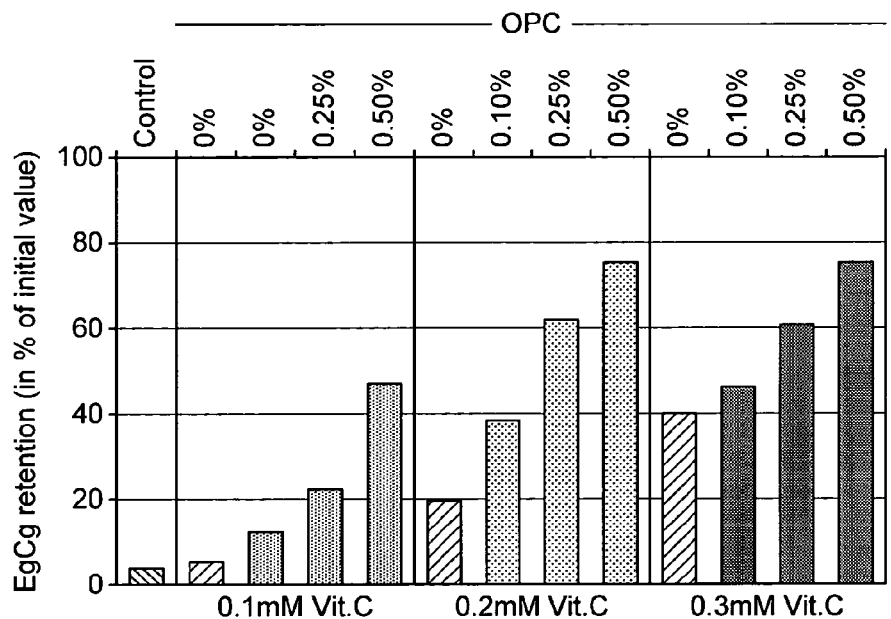
FIG. 1 shows EGCg stabilization during 5 h incubation of green tea in the presence of increasing concentrations of vitamin C and OPC (Indena).

*integration difficult because of elevated concentration of catechin monomers in OPC samples Dose-Response of OPCs+Vitamin C on Catechin Stability In order to optimise vitamin C to OPC ratios for catechin protection, green tea containing three different concentrations of vitamin C (0.1 mM; 0.2 mM and 0.3 mM) has been incubated with increasing amounts of OPC for up to 5 h. Because of its strong instability, EgCg has been selected as the marker compound to evaluate efficiency of protection. As previously observed, the addition of OPC to the incubated samples increased significantly the stability of EgCg compared to the control with vitamin C alone (FIG. 1). The protective effect of OPC was clearly dose dependent and rose continuously with the increase of the initial vitamin C concentration. The increase was however not linear: a 5 times higher dose of OPC did not provoke a 5 times higher protection. The effect of OPC addition was more pronounced at the lowest vitamin C concentration, but in this case the overall protection was also lower resulting only in about 50% of EgCg retention.

Figure 2:
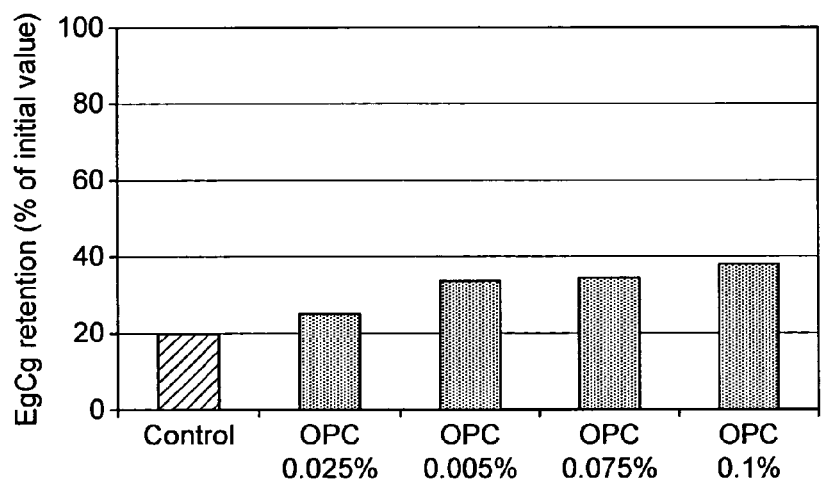
FIG. 2 shows EGCg stabilisation during 5 h incubation of green tea in presence of 0.2 mM vitamin C and increasing concentrations of OPC.

To reduce as far as possible the impact of grape seed catechins on overall catechin profile, a stability test with OPC addition in the range between 0.025% and 0.1% together with 0.2 mM vitamin C was performed. After 5 h incubation, EgCg protection in green tea showed to be dose-dependent and reached a maximum of 40% at 0.1% of OPCs (FIG. 2). The observed increase was not linear; in particular at an OPC concentration of 0.05%, the EgCg protection already corresponds to 75% of that observed with 0.1% OPCs. Finally, this formulation, combining 0.2 mM vitamin C with 0.05% of OPC, has been selected as a good compromise between overall catechin protection and reduced OPC content. It has been tested in a clinical trial to evaluate the effect of VitC/OPCs to improve catechin bioavailability.

Example 2

Bioavailability Study

Material & Methods

Subjects

Twelve men in the age range from 22-46 years old recruited at the NRC were enrolled in the trial. Volunteers were declared healthy after they completed a medical questionnaire and were examined by a physician. No medication, vitamins-minerals supplements were allowed during the study. All subjects were non-smokers. Vegetarian, vegan and men having a regular consumption of more than 3 cups of tea (all type, including herbal tea) per week or 200 g of chocolate per week, including products containing chocolate were excluded from the study. Subjects were fully informed of the aims of the study and given they written, informed consent. The study protocol was approved by the ethical Committee of the CHUV of Lausanne.

Design of the Study

A schematic diagram of the study is shown in FIG. 3. This study was a double-blind cross over design. The product tested was a green tea extract, TCTG (CWS.08), an aqueous extract of green tea leaves produced in Choladi (Nestlé India) and supplied by Givaudan. This green tea extract was used for the four different treatments in the study: They comprise:

Green tea extract (GT) powder (1 g per person)

Green tea extract powder with grape seed extract and Vitamin C (GTCV) (1.535 g of product per person containing 1 g of green tea extract, 0.5 g of grape seed extract and 0.035 g of vitamin C.

Green tea extract powder with two other formulations which won't be further described here.

The four studied products were labelled with the product codes A, B, C and D. The four different treatments were encapsulated in gelatine capsules and administered orally with 300 ml of low mineral water 2 h after the breakfast. 1 g green tea extract per treatment was given to the subjects. The catechins composition of the extract is reported in table 6.

TABLE 6

Catechins profile of green tea extract Ref: 52160450BA (%)

| EGC | Cat | EGCG | EC | ECG | Total |
|---|---|---|---|---|---|
| 12.4 | 0.4 | 17.8 | 2.2 | 3.1 | 35.9 |

Two days before receiving one treatment, subjects were asked to not consume alcohol, flavonoid rich foods and drinks, tea products, herb tea, chocolate products, coffee products, grape juice and more than 250 ml per day of other fruit juices. Their diet was standardized one day before and the day of the experiment. That day subjects came fasting to the Metabolic Unit, where they consumed a light catechin-free breakfast. A catheter was placed in the right or left arm to allow for repeated blood drawing at the intervals described below over 8 hours. Two hours after the breakfast the subjects received one of the 4 treatments A, B, C or D according to the randomization. Blood samples were taken at 0, 30, 60, 90, 120, 180, 240, 360, and 480 min after the absorption of the treatment. 250 ml of physiologic serum (NaCl 0.9%) were infused through the catheter for 6 hours in order to avoid obstruction of the catheter. Before blood sampling, 2 ml of liquid will be removed from the catheter to avoid contamination of the blood samples by NaCl. The subjects had lunch at the Metabolic Unit. A standardized meal will be supplied for the evening. On the morning, the day after a fasting blood sample was taken to complete the pharmacokinetics.

Sample Treatments and Analysis

Each blood sample was centrifuged at 3500 g at 4° C. for 10 min immediately after blood drawing for obtaining plasma. Plasma obtained from this tube was mixed with EDTA and vitamin C. Then, samples were frozen at −80° C. until analysis. The analysis was performed in an external laboratory (Brunswick Laboratories, LLC, Norton, Mass., USA) according to the following protocol. Briefly, thawed plasma was centrifuged (14000 rpm, 5 min, 4° C.) in Eppendorf Centrifuge 5417R. 200 µl of plasma was then mixed with 12 µl of 10% ascorbic acid—40 mM KH2PO4—0.1% EDTA, 20 µl of 50 mM potassium phosphate (pH 7.4), 20 µl of 1.0 µg/ml catechin gallate (CG) as internal standard, 500 units of β-d-glucuronidase type X-A from *E. coli* (Sigma Chemical Co, St. Louis, Mo., USA) and 4 units of sulfatase type VIII from abalone entrails (Sigma Chemical Co). The mixture was incubated at 37° C. for 45 min. The reaction was stopped by the addition of 2 ml of ethyl acetate followed by vigorous shaking for 20 min and centrifugation at 4° C. at 2000×g for 5 min. The supernatant was transferred to a clean tube, and the ethyl acetate extraction was repeated. 10 µl of 0.02% ascorbic acid: 0.005% EDTA was added to the pooled supernatant fraction and vortexed thoroughly to mix. The supernatant was then evaporated to dryness with nitrogen for 2 h at room temperature. The samples were reconstituted in 200 µl of methanol: water (1:2, vol), vortexed well, sonicated for 10 min, and centrifuged (14000 rpm, 5 min, 4° C.). 20 µl of the supernatant was injected into the HPLC system. The HPLC—electrochemical detection (ECD) system consisted of ESA Model 582 solvent delivery system, ESA Model 542 autosampler, an ESA 5600 CoulArrray electrochemical detector (ESA, Bedford, Mass., USA) with CoulArrayWin Software 1.12, Eppendorf CH-30 Column Heater, a C18 Phenomenex guard column, 4.0 mm L×3.0 mm, and a SUPELCO Ascentis RP-Amide column, 15 cm×4.6 mm i.d., 5 µm particles. Standard flavanol solutions and internal standard (catechin gallate) were prepared in a methanol and water (1:2, vol) solution and stored at −70° C. The column was eluted at 35° C. starting at a flow rate of 1 ml/min with 70% buffer A (40 mM ammonia phosphate monobasic, pH adjusted to 3.0 by phosphoric acid) and 30% buffer B (40 mM ammonia phosphate monobasic 50%/L: 50% acetonitrile/L, pH adjusted to 3.0 by phosphoric acid). After one min, the gradient was linearly changed from 70% buffer A and 30% buffer B to 10% buffer A and 90% buffer B (1-10 min), 70% A/30% B (10-12). The eluent was monitored by HPLC-electrochemical detection with potential settings at −30, 100, 230, 400 mV. The dominant channel was at 230 mV.

Results:

Plasma Bioavailability of Epigallocatechin-3 Gallate

For epigallocatechin-3 gallate (EGCG), the limit of quantification was 0.005 µg/mL. The kinetic parameters of epigallocatechin-3 gallate from different treatments are given in Table 7.

TABLE 7

Kinetic parameters of epigallocatechin-3 gallate by treatment (mean ± sd)

| Treatment | Number of subject | $C_{max}$ (µg/mL) | $T_{max}$ (min) | $AUC_{(0-22\,h)}$ (µg/mL * min) |
|---|---|---|---|---|
| [GTVC] | 12 | 0.206 ± 0.053 | 108 ± 30 | 51 ± 15 |
| [GT] | 12 | 0.171 ± 0.079 | 103 ± 20 | 40 ± 12 |
| Relative difference | | +20.5% | | +27.5% |

The addition of grape seed extract and vitamin C to the green tea extract increased the AUC and the Cmax of EGCg by 27.5 and 20.5% respectively. The Tmax was not affected by the mixture.

If $AUC_{(22h-inf.)}$ is smaller than 30% of $AUC_{(0h-inf.)}$, $AUC_{(0h-inf.)}$ and $T_{1/2}$ can be taken into consideration. The $AUC_{(0h-inf.)}$ and $T_{1/2}$ of epigallocatechin-3 gallate from different treatments are given in Table 8.

TABLE 8

$AUC_{(0\,h-inf.)}$ and $T_{1/2}$ of epigallocatechin-3 gallate by treatment (mean ± sd)

| Treatment | Number of subject | $AUC_{(0\,h-inf.)}$ (µg/mL * min) | $T_{1/2}$ (min) |
|---|---|---|---|
| [GTVC] | 12 | 58 ± 15 | 292 ± 134 |
| [GT] | 10 | 46 ± 17 | 241 ± 174 |
| Relative difference | | +26% | +21% |

The mean AUC of these extrapolated kinetic curves of epigallocatechin-3-galate is increased by 26% when the green tea is mixed with the grape seed extract and the vitamin C when compared to the green tea extract (GT) consumed alone. The T1/2 was also increased by 21%.

Plasma Bioavailability of Epicatechin-3-Gallate

For epicatechin-3-gallate, the limit of quantification was 0.005 µg/mL. The kinetic parameters of epicatechin-3-gallate from different treatments are given in Table 9.

TABLE 9

Kinetic parameters of epicatechin-3-gallate by treatment (mean ± sd)

| Treatment | Number of subject | $C_{max}$ (µg/mL) | $T_{max}$ (min) | $AUC_{(0-22\,h)}$ (µg/mL * min) |
|---|---|---|---|---|
| [GTVC] | 12 | 0.15 ± 0.10 | 153 ± 83 | 114 ± 106 |
| [GT] | 11[b] | 0.11 ± 0.08 | 104 ± 39 | 80 ± 79 |
| Relative difference | | +26% | +47% | +42.5% |

In treatments [GT], the data of t subjects "16[b]" are missing.

The co-ingestion of grape seed extract and vitamin C with the green tea extract increased the AUC, the Cmax and the Tmax of ECg by 42.5, 26 and 47%, respectively. If $AUC_{(22h-inf.)}$ is smaller than 30% of $AUC_{(0h-inf.)}$, $AUC_{(0h-inf.)}$ and T1/2 can be taken into consideration. The majority of subjects has $AUC_{(22h-inf.)}>30\%$ of $AUC_{(0h-inf.)}$. The extrapolation can therefore not be performed.

Plasma Bioavailability of Epigallocatechin

For epigallocatechin, the limit of quantification was 0.005 µg/mL.

The kinetic parameters of epigallocatechin from different treatments are given in Table 10.

TABLE 10

Kinetic parameters of epigallocatechin by treatment (mean ± sd)

| Treatment | Number of subject | $C_{max}$ (µg/mL) | $T_{max}$ (min) | $AUC_{(0-22\,h)}$ (µg/mL * min) |
|---|---|---|---|---|
| [GTVC] | 12 | 0.96 ± 0.65 | 120 ± 46 | 238 ± 129 |
| [GT] | 11[b] | 0.81 ± 0.45 | 125 ± 58 | 229 ± 151 |
| Relative difference | | +18.5% | | +3.9% |

In treatments [GT], the data of t subjects "04[b]", "10[c]" and "14[c]" are missing.

The co-ingestion of grape seed extract and vitamin C with the green tea extract increased the AUC and the Cmax of EGC by 3.9 and 18.5% respectively. The Tmax was not affected by the mixture.

If $AUC_{(22h-inf.)}$ is smaller than 30% of $AUC_{(0h-inf.)}$ $AUC_{(0h-inf.)}$ and $T_{1/2}$ can be taken into consideration. These $AUC_{(0h-inf.)}$ and $T_{1/2}$ of epigallocatechin from different treatments are given in Table 11.

TABLE 11

AUC$_{(0\ h-inf)}$ and T$_{1/2}$ of epigallocatechin by treatment (mean ± sd)

| Treatment | Number of subject | AUC$_{(0\ h-inf)}$ (μg/mL * min) | T$_{1/2}$ (min) |
|---|---|---|---|
| [GTVC] | 12 | 252 ± 136 | 211 ± 1123 |
| [GT] | 11 | 257 ± 153 | 259 ± 145 |

The kinetics parameters are not increased when AUC are extrapolated.

Plasma Bioavailability of Epicatechin and Catechin

Comparison for epicatechin and catechin was not possible as the grape seed extract contained 24.3% of total catechin and epicatechin.

CONCLUSION

The bioavailability of the main catechin (EGCg) of green tea extract was been showed to be increased when co-ingested with a mixture of vitamin C and grape seed extract. The same observation was made for ECg.

The invention claimed is:

1. A method for treatment comprising sustaining and/or improving the bioavailability of a catechin in an individual, the method comprising:
   administering to an individual in need of same a composition having an improved bioavailability of a green tea catechin comprising a mixture of grape seed extract in an amount from 10 to 40%, a prophylactic amount of hesperitin, and ascorbic acid or vitamin C analogs, wherein the ascorbic acid or vitamin C analogs are provided in an amount from 0.1% to 15% by weight of the composition, and wherein the green tea catechin is provided in an amount ranging from 5 to 30% by weight of the composition, and the grape seed extract comprises oligomeric procyanidins (OPC) in an amount from 60 to 99%.

2. The method of claim 1, wherein the composition is in a form selected from the group consisting of a food product, a pet food product, a nutritional composition, a nutraceutical, a food supplement, a cosmetic composition, a medicament, and combinations thereof.

3. The method of claim 1, wherein the composition is in a form selected from the group consisting of capsules, gelatin capsules, soft capsules, tablets, sugar-coated tablets, pills, pastes or pastilles, gums, drinkable solutions or emulsions, syrups, gels, and combinations thereof.

4. The method of claim 1, wherein the composition comprises at least one ingredient selected from the group consisting of a sweetener, a stabilizer, a flavoring, a colorant, and combinations thereof.

5. The method of claim 1, wherein the mixture of oligomeric procyanidins (OPC) is provided in an amount ranging from 10 to 40% by weight of the composition.

6. A method for sustaining and/or improving the bioavailability of a green tea catechin in an individual, the method comprising:
   administering to the individual a composition comprising at least one green tea catechin and a mixture of grape seed extract in an amount from 10 to 40%, a prophylactic amount of hesperitin, and ascorbic acid or vitamin C analogs, wherein the ascorbic acid or vitamin C analogs are provided in an amount from 0.1% to 15% by weight of the composition, the green tea catechin is provided in an amount ranging from 5 to 30% by weight of the composition, and the grape seed extract comprises oligomeric procyanidins (OPC) in an amount from 60 to 99%.

7. The method of claim 6, wherein the composition is in a form selected from the group consisting of a food product, a pet food product, a nutritional composition, a nutraceutical, a food supplement, a cosmetic composition, a medicament, and combinations thereof.

8. The method of claim 6, wherein the composition is in a form selected from the group consisting of capsules, gelatin capsules, soft capsules, tablets, sugar-coated tablets, pills, pastes or pastilles, gums, drinkable solutions or emulsions, syrups, gels, and combinations thereof.

9. The method of claim 6, wherein the composition comprises at least one ingredient selected from the group consisting of a sweetener, a stabilizer, a flavoring, a colorant, and combinations thereof.

10. The method of claim 6, wherein the mixture of oligomeric procyanidins (OPC) is provided in an amount ranging from 10 to 40% by weight of the composition.

* * * * *